United States Patent [19]

Emrich

[11] 4,163,039
[45] Jul. 31, 1979

[54] DIAGNOSTIC MEANS FOR THE RAPID DETECTION OF MUCOVISCIDOSIS

[76] Inventor: Hinderk M. Emrich, Lortzingsstrasse 16, D-8011 Vaterstetten, Fed. Rep. of Germany

[21] Appl. No.: 868,556

[22] Filed: Jan. 11, 1978

[51] Int. Cl.² ............................................. G01N 33/16
[52] U.S. Cl. .................................. 422/56; 23/230 B; 422/58
[58] Field of Search ........................ 23/230 B, 253 TP

[56] References Cited

U.S. PATENT DOCUMENTS

| | | | |
|---|---|---|---|
| 3,449,080 | 6/1969 | Edwards | 23/230 B |
| 3,605,722 | 9/1971 | Riseman | 23/230 B |
| 3,902,847 | 9/1975 | Busch | 23/253 TP |

Primary Examiner—Sidney Marantz
Attorney, Agent, or Firm—Sprung, Felfe, Horn, Lynch & Kramer

[57] ABSTRACT

Mucoviscidosis is rapidly detected by determining the sodium or chlorine concentration in the sweat secretions of the subject by diagnostic means comprising an absorbent support impregnated with an indicator substance for indicating sodium or chlorine ions by way of a color change and capable of producing a plainly visible color when the sodium or chlorine ion concentration is at least 50 mval/l of absorption volume, and a transparent envelope which seals in the color indicating substance on all sides of said absorbent support, and which is perforated on one flat side to permit absorption of sweat directly from the skin surface of the subject.

12 Claims, 4 Drawing Figures

DIAGNOSTIC MEANS FOR THE RAPID DETECTION OF MUCOVISCIDOSIS

The invention relates to a diagnostic means which permits the rapid and simple detection of mucoviscidosis (cystic fibrosis of the pancreas).

Mucoviscidosis is a disease whose symptoms are caused by a dysfunction of exocrine glands, in which there is an increase in the viscosity of the mucoid secretions, affecting mainly the excretory cells of the pancreas in addition to the bronchial mucous glands. The secretory disturbances caused by the greatly increased viscosity of the secretion lead to severe disease symptoms. In children suffering from this disease, failure to diagnose it early leads to great danger. Consequently, there is a great need for a means which will permit the rapid diagnosis of mucoviscidosis, and especially which will make possible the routine testing of newborn infants.

A variety of methods for the diagnosis of mucoviscidosis are already known. These methods determine abnormal protein digestion, for example, by what is known as the film digestion test, or the abnormal digestion of fats by means of oily complex compounds. These test methods, however, are expensive and unspecific.

Other methods are based on the fact that, in mucovissidosis, there is a considerably elevated salt content in the eccrine sweat. The secretion of sweat is provoked in various ways, and the sodium chloride content is determined in the sweat. One of these methods is an agar plate test in which an agar plate containing suspended silver chromate is used as the diagnostic means. The silver chromate discolors in the presence of sodium chloride through the formation of silver chloride at the points where discoloration occurs. The degree of color change gives an approximate indication of the sodium chloride concentration. This test, however, is rather difficult and the results leave much to be desired in regard to reliability, since precise quantification is impossible.

A further development of this test uses a prepared paper strip instead of the agar plate. The results achieved, however, do not permit a reliable diagnosis of mucoviscidosis, since positive test results have been encountered in healthy subjects, and only a negative test result excludes the presence of mucoviscidosis. Consequently, if the test results were positive, it was necessary to ascertain by other methods whether or not the subject really had the disease.

In one generally recognized, reliable method of determination, pilocarpine was first introduced into the skin by iontophoresis, then the skin was cleaned, and then a piece of filter paper of determined weight was laid on it; the paper was covered with a plastic film, and fastened down with adhesive tape. After the sweat had been absorbed over a 30 minute period, the paper was reweighed. Then a chlorine determination was made in the eluate by conventional methods. The amount of chlorine measured afterwards made it possible to determine the concentration of the sodium chloride in the sweat on the basis of the difference in weight. This expensive and time-consuming method does give very precise results, but precision of this kind is not at all needed for the reliable diagnosis of mucoviscidosis. It appears, for example, from the dissertation of H. M. Emrich at the University of Bern of 1967, p. 61, that the difference in sodium chloride concentration between normal subjects and those suffering mucoviscidosis is very great. For example, the chlorine ion concentration in the healthy subject is mostly less than 20 mval/l, and only in odd cases is it between 20 and 40 mval/l. In mucoviscidosis patients, however, the concentration as a rule is between 80 and 140 mval/l, and only in exceptional cases is it between 60 and 80 mval/l. A reliable method for the determination of mucoviscidosis therefore needs only to make it possible to determine that the chlorine ion concentration exceeds 50 mval/l. For sodium ions, the corresponding values in the healthy subject are as a rule less than 40, and in exceptional cases they are between 40 and 60 mval/l, and in sufferers of the disease they are also as a rule higher than 80 mval/l. In this case, therefore, the reliable detection of a sodium ion concentration above 60 mval/l would be necessary.

It is the object of the invention, therefore, to create a high-speed diagnostic means which will not have the disadvantages of the known methods and diagnostic means, and which on the other hand will reliably indicate whether the above-stated limits of the sodium chloride concentration are exceeded.

This object is achieved by the invention by a means for the rapid diagnosis of mucoviscidosis by determining the sodium or chloride concentration in sweat, which is characterized by an absorbent support in leaf form, a substance indicating sodium or chlorine ions by color change, in an amount which is correlated with the absorption volume of the support and produces a plainly visible color change when the sodium or chlorine ion concentration amounts to at least 50 mval/l of absorption volume, and by a transparent envelope which seals the color changing substance in on all sides and which is perforated on one of its two flat sides such that the absorbent support can absorb the sweat directly from the surface of the skin.

The absorbent support in leaf form can be, for example, absorbent paper, porous plastic or the like. Suitable absorbent support materials in leaf form are known.

Those substances can be used as substances indicating chloride ions or sodium ions by color change (indicators) which show a definite color change when they have reacted completely with these ions. Examples of suitable compounds are silver chromate, which is preferred, and other colored silver salts or mercury salts whose solubility product markedly exceeds that of silver chloride or mercury chloride. Additional examples of suitable indicators for chlorine ions are the mercury thiocyanate-iron reaction and the diphenylcarbazone- or 2-(8-hydroxyquinolyl-5-azo)-benzoic acid reaction.

In accordance with an additional embodiment of the invention, the chloride ion detection can be performed by the activation of α-amylase by chlorine ions. The substance producing a color change in the presence of chlorine ions in this case consists of α-amylase and potassium iodide starch. The α-amylase activated by the chloride ions decomposes the starch, so that the characteristic coloration of the iodine-starch complex vanishes.

The absorbent support can already contain the color reagent, i.e., it can be impregnated with the color reagent, which can be understood also as a mixture of several substances. Alternatively, it is also possible to separate the absorbent support from the color reagent by a removable partition which can be removed after the necessary amount of sweat has been absorbed. Such a removable partition can consist, for example, of a transparent film of plastic, which can be removed from the diagnostic means, or of a substance that can be broken by pressure.

A first and preferred embodiment of the high-speed diagnostic means of the invention consists of the absorbent support in leaf form, which is impregnated with such an amount of silver chromate that, when the absorption volume has been completely filled with sweat, no discoloration of the silver chromate is produced by the amounts of sodium chloride which are present in healthy sweat, i.e., less than 50 mval., but if this limit of the sodium chloride concentration is exceeded, complete discoloration takes place.

In order to make sure that the absorbent support has been completely filled with sweat, an additional reagent can be provided at a point on the support farthest removed from the point of absorption, which will indicate by color change that the sweat has reached that point. Suitable reagents for this purpose are, for example, salts which, in the anhydrous state, have a different color from that which they have in the hydrated state, such as for example copper sulfate, which is white in the anhydrous state, but turns blue when it is hydrated.

An especially simple embodiment of the diagnostic means of the invention can be obtained by impregnating an absorbent paper with the color-changing substance, drying it, and then applying to it a plastic film coated with an adhesive. This plastic film is then covered on the other side with a second film, which is perforated but should not be covered with an adhesive coating, such that a sufficiently large margin remains around the actual filter paper to assure the complete sealing in of the filter paper by the two cover films. Optionally, of course, the two films could also be welded at the margin, so that an adhesive coating can be dispensed with. The shape of the absorbent strip can be as desired, but an approximately circular shape is preferred, since this creates the most favorable conditions with regard to the uniform absorption of the volume of sweat. If a second indicator substance is provided to indicate the progress of the sweat, the circular leaf of filter paper can have a tab on its circumference which is impregnated with this second substance. Instead of this, a second filter paper can also be impregnated with the second indicator substance and can be laid on the periphery of the first filter paper, or can be cemented or otherwise fastened thereto. Also, the paper impregnated with the sweat indicating substance can be of annular shape and can be laid on the periphery of the actual absorbent support. Instead, however, it is also possible, of course, to impregnate with this second indicator substance a marginal area of the first support in which the sweat is absorbed.

In another embodiment of the invention, the absorbent support has a plurality of zones impregnated with different amounts of color indicator. In this manner a semi-quantitative determination can be performed. This can be accomplished in a circular absorbent support, for example by impregnation in the form of sectors, these sectors being impregnated with different amounts of color indicator. For example, a sector can be designed for a color change at 40 mval/l of chloride ions, another for a color change at 70 mval/l and a third for a color change at 100 mval/l, by impregnating only these sectors with the amount of color indicator required in each case. The individual sectors can consist of separate pieces of support material put together in circular form.

If the absorbent support is of rectangular shape, it is best to arrange the zones of different degrees of impregnation in the form of parallel strips, or in checkerboard pattern, or the like.

The embodiment of the diagnostic means of the invention comprising a partition between the actual absorbent support and the indicator substance can have, for example, two absorbent support sheets which are separated from one another by a removable film. The purpose of the first support is to absorb the sweat, and the second absorbent support is impregnated with the indicator substance. As soon as the first absorbent support is saturated with sweat, the intermediate film is pulled out and the color reaction can take place. Optionally, a breakable capsule containing a solution of the indicator substance can also be provided, and as soon as the absorbent support is saturated with sweat, this capsule is broken by the application of pressure, so that the reaction with the chloride ions or sodium ions in the sweat can take place.

In the additional embodiment mentioned above, in which α-amylase and iodine-potassium iodide starch are used as color indicator, a fading of the color takes place, the rate of which depends on the chloride ion concentration. In this embodiment, the indicator reagent can be provided, for example, in a separate capsule which is opened after the absorbent support is saturated, so that rapid contact takes place between the indicator solution and the sweat. Then, by means of a stop watch, the time it takes for the fading to take place is measured. In this manner a semi-quantitative result is obtained, which permits the determination of the chloride ion concentration with an accuracy of 10 to 20 mval.

The appended drawing will serve for the further explanation of the invention.

Figure 1:
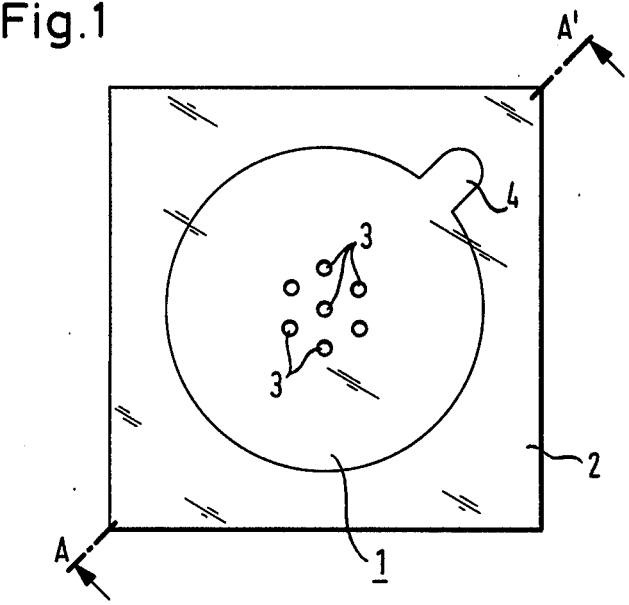
FIG. 1 is a plan view of a diagnostic means of the invention.

As FIG. 1 shows, a high-speed diagnostic means of the invention consists of a circular leaf of filter paper 1, having a diameter of 1 cm. The round filter paper leaf 1 is impregnated with silver chromate in such an amount that a color change will occur when the chloride ion concentration exceeds 50 mval per liter of absorption volume. The absorption volume can easily be determined by weighing in the dry and in the sweat-impregnated state, and the required amount of silver chromate color indicator can be determined in the same manner. The impregnated filter paper leaf 1 is surrounded by a transparent plastic envelope 2. This has on one side a perforation 3 which is situated above the center of the circular leaf 1. The circular leaf 1 also has a tab 4 which is impregnated with anhydrous copper sulfate.

In use, the diagnostic means of FIG. 1 is laid upon the skin which has been prepared in the usual way for the excretion of sweat, which is best provoked by pilocarpine iontophoresis. Optionally, it is also possible to inject subcutaneously cholinergics such as ACh, carbachol and the like, or, if desired, physostigmine.

The diagnostic means is then laid on the skin with the perforated side toward the skin, and is best fastened down with adhesive tape. As soon as the tab 4 begins to turn blue, the diagnostic means is removed again from the skin, and examined to determine whether the color change from dark gray to light gray has taken place in the circular support.

Figure 2:
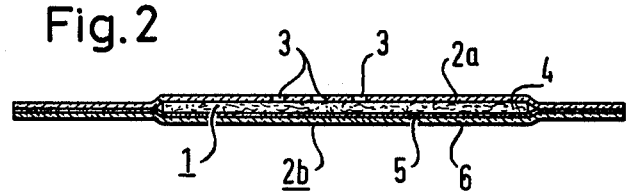
FIG. 2 is a cross-sectional view of the diagnostic means, taken along line A-A' of FIG. 1.

FIG. 2 shows the diagnostic means of FIG. 1 in a cross section on line A-A' and shows additional details of its construction. The filter paper disk 1 is covered by a transparent film 2a having perforations 3 disposed over the center of the circular disk 1. The other side of the filter paper leaf 1 is covered by a second transparent plastic film 2b, which in turn consists of a coat of adhesive 5 and the actual plastic film 6. The films 2a and 2b extend all the way to the margin beyond the filter paper leaf and are there tightly held together by the adhesive coating 5.

Figure 3:
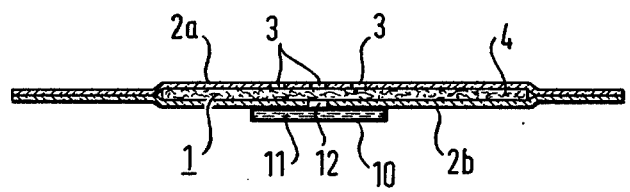
FIG. 3 is a lateral cross section of another embodiment of the diagnostic means of the invention.

Another embodiment of the diagnostic means of the invention is shown in FIG. 3. The plan view of this embodiment is the same as that shown in FIG. 1. In this case, however, the filter paper leaf 1 is not impregnated. The two cover films 2a and 2b are welded together at the outer margin, and there is no adhesive coating 5. Opposite the perforation 3, on the back film 2b, there is provided a capsule 10 filled with a solution 11 of -amylase and iodine-potassium iodide starch. The back film 2b has an aperture 12 at the point covered by the capsule 10. By the application of pressure to the capsule 10, the partition separating it from the film 2b is broken, so that the solution 11 flows through the aperture 12 and comes in contact with the filter paper leaf 1 which is already saturated with sweat. Then the time is determined which it takes for the color to fade. This time is an index of the chloride ion concentration.

EXAMPLES

The following examples will further explain the invention.

EXAMPLE 1

50 mg of agar is dissolved in 100 ml of boiling distilled water. First, 0.85 g of $AgNO_3$, and then 0.425 g of $KCrO_4$ are added to the solution while it is still hot. 200 microliters of the still warm solution thus obtained is placed on a piece of filter paper (Schott) of 50 mm diameter, and evenly distributed thereon. Then the paper is dried. Circular disks of 5 mm diameter are punched from the dried paper. The disks are inserted into a filter paper sheet 15×15 mm, in the center of which a hole 5 mm in diameter has been punched. The filter paper is then adhered to Tesafilm and placed in a wrapper of transparent plastic self-adhesive tape.

A pilocarpine iontophoresis is performed on a patient whose skin is then washed with a detergent, rinsed with distilled water, and dried. The diagnostic strip is adhered to the skin area thus prepared. As soon as the uncolored filter paper sheet into which the colored round filter paper disk is inserted indicates the absorption of sweat, the strip is removed and examined to see whether a fading of the color from dark gray (slate gray) to light gray (silver gray) has taken place.

The following table shows the results obtained in a series of experimental subjects with and without mucoviscidosis, in comparison with the sodium ion concentrations determined by other methods. It can be seen that, in all cases, no fading of color occurred in healthy persons, while it did occur in all cases of mucoviscidosis.

TABLE

| Patient | Diagnosis | $Na^+$ (mval/l) | Decoloration |
|---|---|---|---|
| P. J. | Mucoviscidosis | 98 | ++ |
| H. J. | " | 74 | + |
| K. J. | " | 140 | ++ |
| Sch. R. | " | 100 | ++ |
| S. B. | " | 104 | ++ |
| S. N. | " | 108 | ++ |
| K. Sch. | " | 100 | ++ |
| M. J. | negative | 18 | — |
| K. T. | " | 20 | — |
| B. K. | " | 26 | — |
| F. R. | " | 24 | — |
| S. O. | " | 22 | — |
| W. S. | " | 16 | — |
| F. R. | " | 24 | — |

EXAMPLE 2

A color indicator solution was prepared, which contained 150 mg/ml of starch and $10^{-2}$ M/l I-KI. The pH was 6.85.

As described in Example 1, a diagnostic means was prepared, in which, however, the circular filter paper disk was not impregnated. The absorptive capacity of the disk was determined to be 100 microliters. 10 microliters of the above I-IK starch solution was placed in a thin glass capillary and the capillary was sealed and affixed to the filter paper disk with Tesafilm. By a light pressure with the thumb the capillary could be broken thus starting the color fading reaction. The rate at which the fading took place was then measured.

Figure 4:
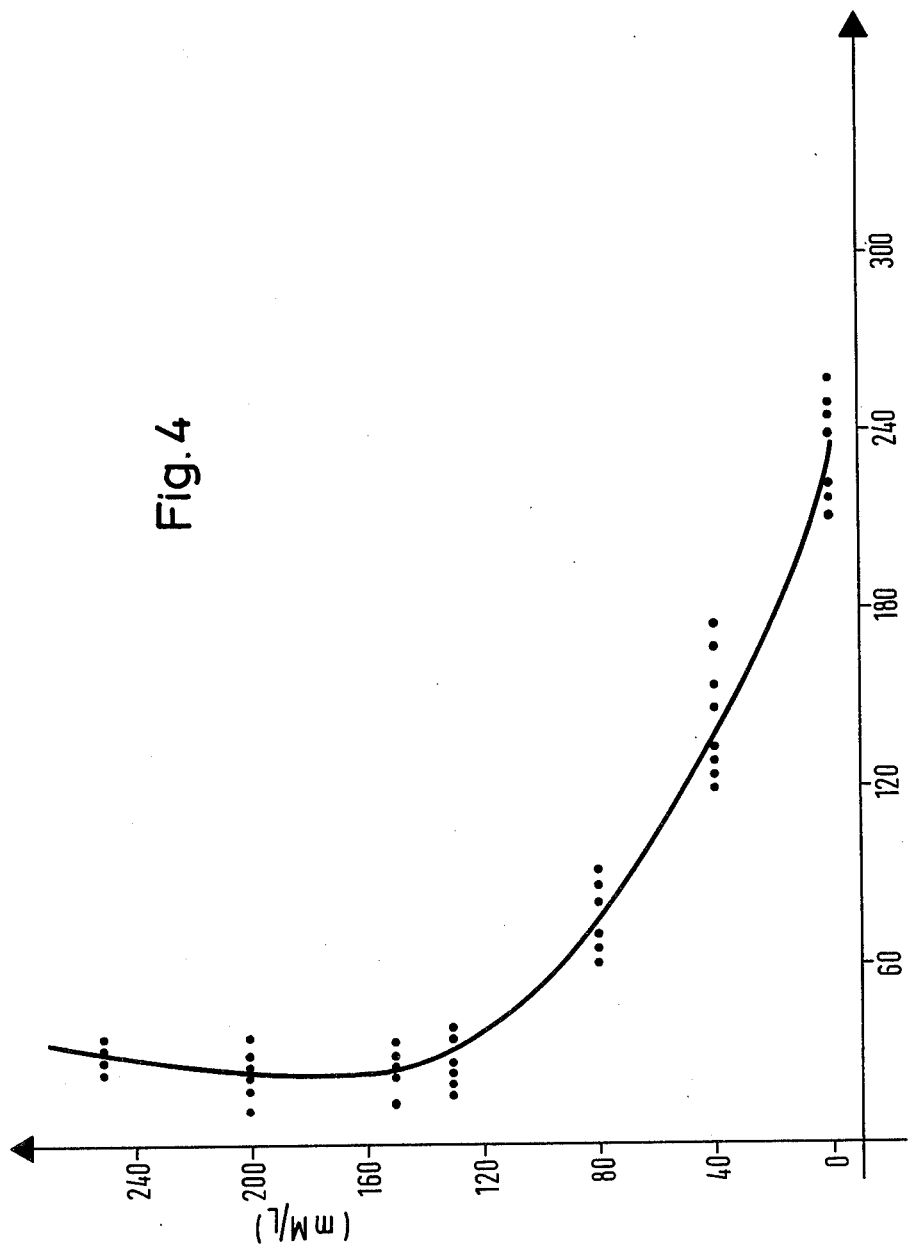
FIG. 4 is a calibration curve for the determination of the chloride ion concentration using α-amylase and iodine-potassium iodide starch as the color indicator substance.

FIG. 4 in the drawing is a graphic representation of the fading time in relation to the chloride concentration.

It will be understood that the specification and examples are illustrative but not limitative of the present invention and that other embodiments within the spirit and scope of the invention will suggest themselves to those skilled in the art.

What is claimed is:

1. Diagnostic means for the rapid detection of mucoviscidosis, comprising
   (1) an absorbent sheet,
   (2) an indicator associated with said sheet, said indicator producing a color change when the diagnostic means is contacted by a subject's sweat having a concentration of sodium or chloride ions of at least 50 meq./l; and
   (3) a transparent envelope which envelops the indicator-associated sheet, said envelope being perforated on one surface to permit absorption of sweat directly from the skin surface of the subject into said absorbent sheet.

2. Diagnostic means as claimed in claim 1 additionally comprising a sweat indicator material disposed at a point within the transparent envelope removed from said perforations, which indicates, by way of a color change, a contact between said absorbent sheet and sweat, and which is different from the substance indicating the sodium or chlorine ions.

3. Diagnostic means as claimed in claim 1 wherein said absorbent sheet is impregnated with said indicator indicating chlorine or sodium ions.

4. Diagnostic means as claimed in claim 1 wherein said absorbent sheet is separated from said indicator indicating sodium or chlorine ions by a removable partition.

5. Diagnostic means as claimed in claim 1 wherein said indicator is a chlorine ion indicator and comprises iodine-potassium iodide starch, together with alpha-amylase.

6. Diagnostic means as claimed in claim 1 wherein said indicator is a chlorine ion indicator comprising a silver salt whose solubility product is substantially higher than that of silver chloride.

7. Diagnostic means as claimed in claim 1 wherein said indicator is a chlorine ion indicator comprising a mercury salt whose solubility product is substantially higher than that of mercury chloride.

8. Diagnostic means as claimed in claim 1 wherein said indicator is a chlorine ion indicator comprising mercury thiocyanate-iron (III).

9. Diagnostic means as claimed in claim 1 wherein said indicator is a chlorine ion indicator comprising mercury thiocyanate/Hg (II).

10. Diagnostic means as claimed in claim 1 wherein said indicator is a chlorine ion indicator comprising diphenylcarbazone.

11. Diagnostic means as claimed in claim 1 wherein said indicator is a chlorine ion indicator comprising 2-(8-hydroxyquinolyl-5-azo)-benzoic acid.

12. Diagnostic means as claimed in claim 1 wherein said absorbent sheet is leaf-shaped and has tab means at one side.

* * * * *